(12) United States Patent
Brittain, IV et al.

(10) Patent No.: US 11,531,034 B2
(45) Date of Patent: Dec. 20, 2022

(54) COMPOSITIONS AND METHODS FOR LYSIS OF RED BLOOD CELLS

(71) Applicant: Beckman Coulter, Inc., Brea, CA (US)

(72) Inventors: George C. Brittain, IV, Miami, FL (US); Sergei Gulnik, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 478 days.

(21) Appl. No.: 16/611,700

(22) PCT Filed: May 7, 2018

(86) PCT No.: PCT/US2018/031411
§ 371 (c)(1),
(2) Date: Nov. 7, 2019

(87) PCT Pub. No.: WO2018/208681
PCT Pub. Date: Nov. 15, 2018

(65) Prior Publication Data
US 2021/0140984 A1 May 13, 2021

Related U.S. Application Data

(60) Provisional application No. 62/503,202, filed on May 8, 2017.

(51) Int. Cl.
*G01N 33/80* (2006.01)

(52) U.S. Cl.
CPC .................................. *G01N 33/80* (2013.01)

(58) Field of Classification Search
CPC .......................... G01N 33/80; G01N 33/56966
See application file for complete search history.

(56) References Cited

U.S. PATENT DOCUMENTS

| | | | |
|---|---|---|---|
| 4,436,821 A | 3/1984 | Ryan | |
| 4,801,549 A | 1/1989 | Cremins et al. | |
| 5,389,549 A | 2/1995 | Hamaguchi et al. | |
| 2010/0267075 A1 | 10/2010 | Sethu et al. | |
| 2019/0187136 A1* | 6/2019 | Khuu-Duong | ... G01N 33/54326 |

FOREIGN PATENT DOCUMENTS

| | | |
|---|---|---|
| CN | 110770587 | 2/2020 |
| EP | 2177911 A1 | 4/2010 |
| IN | 201917050490 | 1/2020 |
| JP | H07309767 | 11/1995 |
| JP | 2557837 | 11/1996 |
| JP | 2635142 | 7/1997 |
| JP | 2001524665 | 12/2001 |
| JP | 2004503745 | 2/2004 |
| JP | 2007532875 | 11/2007 |
| JP | 2009511001 | 3/2009 |
| JP | 2011505011 | 2/2011 |
| JP | 2013205205 | 10/2013 |
| JP | 2020519873 | 7/2020 |
| JP | 7042845 B2 | 3/2022 |
| WO | WO-8505450 A1 | 12/1985 |
| WO | WO-2018208681 A1 | 11/2018 |

OTHER PUBLICATIONS

Collier et al. Some problems in the use of Coulter counter for erythrocyte total counts and volume distribution. J. Clin. Path. 21: 179-182 (1968).*
"International Application Serial No. PCT/US2018/031411, International Search Report dated Aug. 9, 2018", 4 pgs.
"International Application Serial No. PCT/US2018/031411, Written Opinion dated Aug. 9, 2018", 6 pgs.
"Australian Application Serial No. 2018266361, Response filed Mar. 1, 2022 to Subsequent Examiners Report dated Oct. 21, 2021", 8 pgs.
"Australian Application Serial No. 2018266361, Response filed Oct. 19, 2021 to First Examination Report dated Mar. 15, 2021", 8 pgs.
Japanese Application Serial No. 2019-561720, with English claims, 14 pages.
"International Application Serial No. PCT/US2018/031411, International Preliminary Report on Patentability dated Nov. 21, 2019", 8 pgs.
"Indian Application Serial No. 201917050490, First Examination Report dated Nov. 27, 2020", w/ English Translation, 5 pgs.
"Australian Application Serial No. 2018266361, First Examination Report dated Mar. 15, 2021", 4 pgs.
"Canadian Application Serial No. 3,063,144, Office Action dated Mar. 18, 2021", 5 pgs.
"Canadian Application Serial No. 3,063,144, Response filed Jul. 15, 2021 to Office Action dated Mar. 18, 2021", 15 pgs.
"Japanese Application Serial No. 2019-561720, Office Action dated Aug. 25, 2021", with English translation, 14 pages.
"Australian Application Serial No. 2018266361, Subsequent Examiners Report dated Oct. 21, 2021", 4 pages.

\* cited by examiner

*Primary Examiner* — Gailene Gabel
(74) *Attorney, Agent, or Firm* — Schwegman Lundberg & Woessner, P.A.

(57) ABSTRACT

This disclosure provides methods and kits for lysing red blood cells from whole blood.

12 Claims, 12 Drawing Sheets

COMPOSITIONS AND METHODS FOR LYSIS OF RED BLOOD CELLS

RELATED PATENT APPLICATION

This application is a U.S. National Stage Filing under 35 U.S.C. 371 from International Application No. PCT/US2018/031411, filed on May 7, 2018, and published as WO 2018/208681 on Nov. 15, 2018, which application claims the benefit of U.S. provisional patent application No. 62/503,202, filed on May 8, 2017, which applications are incorporated herein by reference in their entirety.

FIELD OF THE INVENTION

This invention relates to methods and compositions for lysing red blood cells.

BACKGROUND OF THE INVENTION

Red blood cells (RBCs) exist at a 1000:1 ratio to white blood cells (WBCs) in endogenous whole-blood samples, which renders the WBC population a rare event in whole blood. In order to properly analyze WBCs in whole-blood samples by flow cytometry, the RBCs need to first be eliminated in order to concentrate the WBC population and provide meaningful data from the acquisition.

Current RBC lysis methods, which involves hypotonicity, salt, pH changes, detergents, and even modifications of RBC enzymatic activity to induce internal pH and volume changes, have serious drawbacks. Lysis methods based on hypotonicity often produce inconsistent results and can cause the rupture of some WBC populations (primarily granulocytes). As a result, the method often induces alterations in cell activation states and causes alterations in the light-scattering profiles of the WBC populations. Salt-based lyses, such as $NH_4Cl$-based lyses, are slow and can be greatly affected by serum components. These methods often require very large volumes and prolonged incubation time to achieve complete lysis which may cause increased cell death. In addition, salt-based lyses are often accompanied with rapid pH changes, which can be damaging to cellular epitopes and WBCs. Detergent-based lyses are often ineffective with aged samples. Detergents are expensive and also have a wide range of lot-to-lot variations. In fact, very few detergents can lyse the RBCs without also lysing the WBCs (e.g., some saponins). Lysis methods that rely on the metabolism of the red blood cells have donor-to-donor variability and may also be ineffective on aged specimens.

In addition, many of these current methods often require a variety of specialized buffers and thus are difficult to be used in work-flow automation for blood-based samples. The differences in solution viscosities of the buffers used may compromise the ability of the instruments to accurately measure the volumes dispensed or the cell counts. These methods often use large volumes of buffer and thus may also require centrifugation of the sample after lysis in order to reduce the sample volume.

BRIEF SUMMARY OF THE INVENTION

This invention enables rapid lysis of RBCs in whole blood samples under isotonic, neutral pH conditions. The disclosure provides a method of lysing red blood cells comprising: contacting a sample comprising red blood cells and white blood cells with a first buffer comprising a fixative to form a first mixture, the solute concentration of the first buffer being greater than the solute concentration of the sample; and adding a second buffer to the first mixture, formed by the sample and the first buffer, to form a second mixture, wherein the solute concentration in the second mixture is substantially the same as the solute concentration of the sample and whereby the red blood cells in the sample are lysed.

In some embodiments, the sample is a whole blood sample.

In some embodiments, the method further comprises, before adding the second buffer, adding a calcium chelator to block calcium-dependent transport in the red blood cells by chelating calcium. In some embodiments, the first buffer further comprises a calcium chelator.

In some embodiments, the contacting step further includes incubating the first mixture for a period between about 0.5 minutes and about 20 minutes. In some embodiments, the method further includes incubating the second mixture for a second period between about 0.5 minutes and about 20 minutes. In some embodiments, the second buffer includes about 0× to about 1×PBS, e.g., about 0.9× to 1×PBS.

In some embodiments, the first mixture includes about 0.5-3%, e.g., 1.6% formaldehyde, 0.5-20 mM EDTA, e.g., 5 mM EDTA, and 1.2-1.8×PBS, e.g, 1.5× phosphate buffered saline (PBS). In some embodiments, the first buffer includes about 3.2% formaldehyde, about 10 mM EDTA, and about 323 mM salt at about pH 7.4. In some embodiments, the first buffer includes about 2×PBS. In some embodiments, the contacting step includes mixing the first buffer in a 1:1 volume ratio with the sample.

Also provided in this disclosure is a method of processing a whole blood sample comprising: forming a first mixture consisting essentially of a sample of whole blood, a fixative, a hypertonic buffer, and a calcium chelator, wherein the solute concentration of the hypertonic saline is greater than the solute concentration of the whole blood; and adding a second buffer to the first mixture to form an isotonic second mixture.

In some embodiments, the first mixture includes about 0.5%-3% formaldehyde and/or about 0.5-20 mM EDTA. In some embodiments, the second mixture includes about 0.01-2% formaldehyde. In some embodiments, the second buffer is about 0.5-1.5×PBS. In some embodiments, the method further comprises staining cells of the second mixture and introducing the stained cells into a cytometer.

Also provided in this disclosure is a red blood cell lysis kit comprising: a first reagent consisting essentially of hypertonic saline, about 3.2% formaldehyde, and about 10 mM EDTA, wherein the solute concentration of the first reagent is greater than the solute concentration of a whole blood sample; and a second reagent including about 0.9× to about 1×PBS.

In some embodiments, the hypertonic saline in the red blood cell lysis buffer has a salt concentration of about 323 mM and is at pH 7.4. In some embodiments, the second reagent includes about 0.9×PBS.

In some embodiments, the method of lysing red blood cells as described herein is an in vitro method. In some embodiments, the method of lysing red blood cells as described herein is not practiced on human or animal body. In some embodiments, the sample containing red blood cells is an ex vivo sample containing red blood cells.

DETAILED DESCRIPTION

Figure 1:
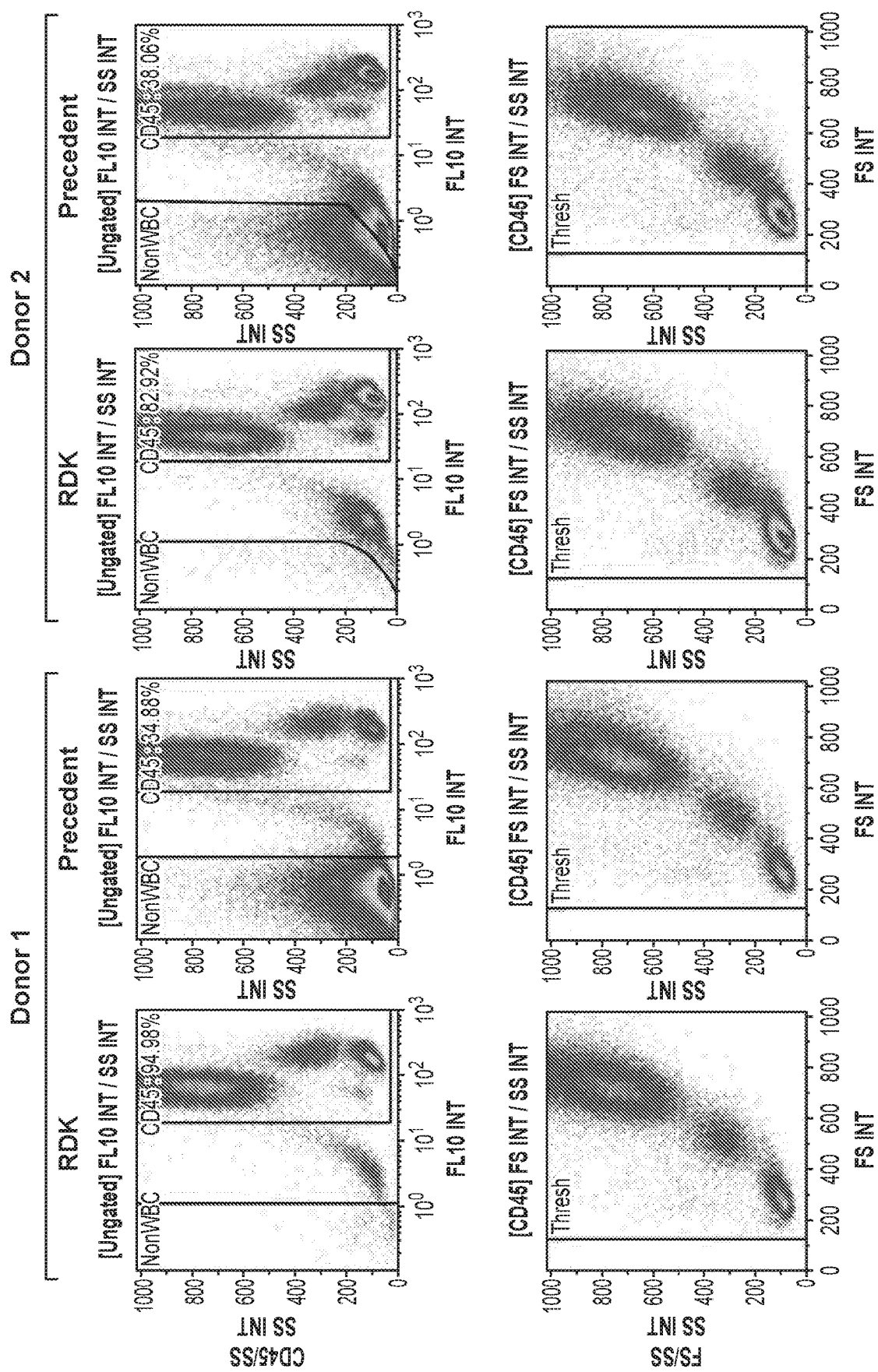
FIG. 1 shows the results of flow cytometry analysis of a 3-Donor Panel, comparing the results of RBC lysis using the Red Blood Cell Demolition Kit ("RDK") disclosed herein versus using the a commercially available buffer system ("precedent buffer").
Figure 1:
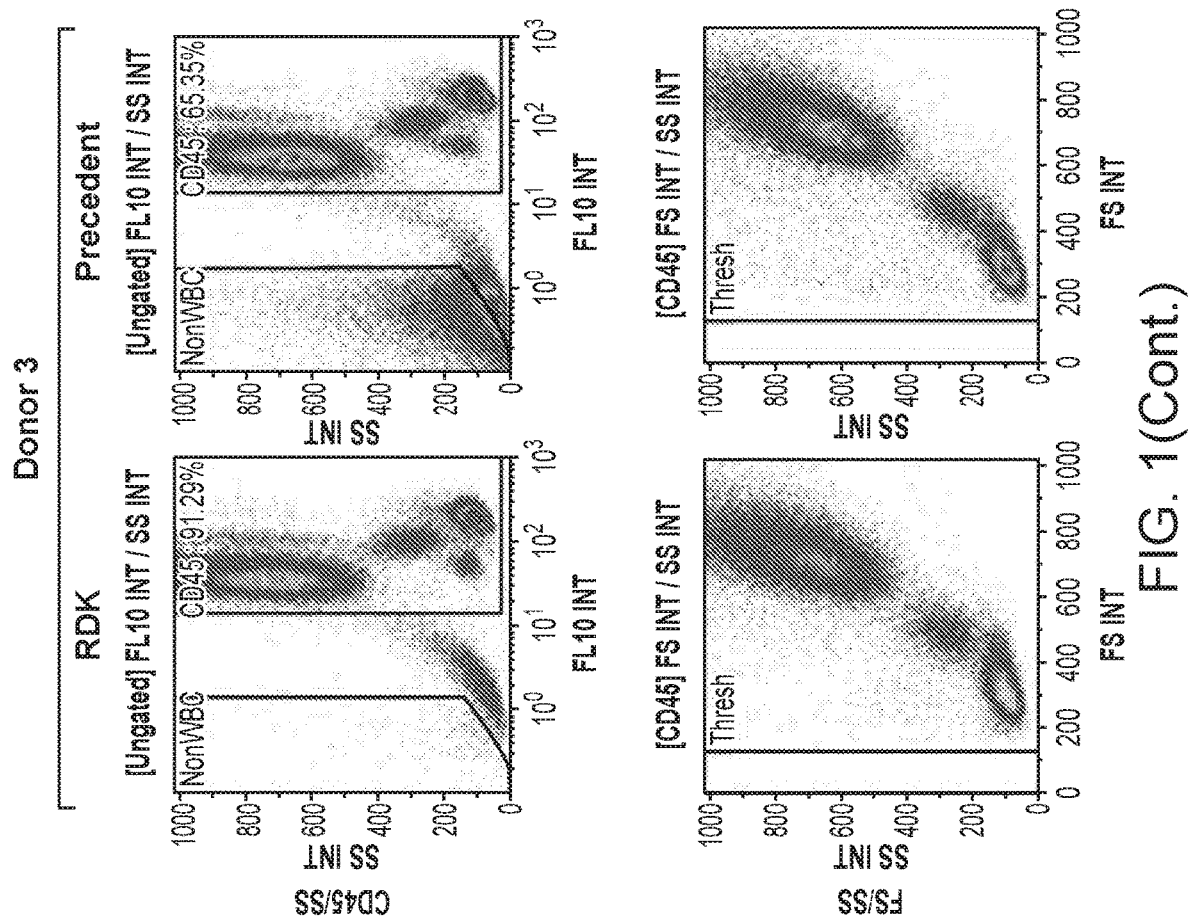

In the description that follows, a number of terms are used extensively, the following definitions are provided to facilitate understanding of various aspects of the invention. Use of examples in the specification, including examples of terms, is for illustrative purposes only and is not intended to limit the scope and meaning of the embodiments of the invention herein. Numeric ranges are inclusive of the numbers defining the range, in the specification, the word "comprising" is used as an open-ended term, substantially equivalent to the phrase "including, but not limited to," and the word "comprises" has a corresponding meaning.

The term "about" when used in conjunction with a value, for example, about 300 mM means a value reasonably close to the value, i.e., within the range of ±5% of the value. In particular, it would include the value itself.

The term "substantially the same" refers to the fact that a first value is almost identical to a second value, and the difference between the two values are insignificant for intended purposes, e.g., the difference between the two values is less than 10%, less than 9%, less than 8%, less than 5%, less than 4%, or less than 2% of the greater value of the two. Stated differently, the solute concentration of a liquid A (mixture or buffer) being substantially the same as the solute concentration of a liquid B, refers to that the solute concentration of the liquid A is at least 90%, at least 91%, at least 92%, at least 95% at least 96%, at least 98%, e.g., 100%, of the solute concentration of liquid B.

In this disclosure, a concentration range listed or described as being useful, suitable, or the like, is intended that any and every concentration within the range, including the end points, is to be considered as having been stated. For example, a range "from 100 mM to 300 mM" is to be read as indicating each and every possible number along the continuum between about 100 mM and about 300 mM.

The terms "ACD blood", "heparin blood", and "K3-EDTA blood" refer to blood samples treated with anticoagulant citrate dextrose, heparin, and K3-EDTA, respectively.

Unless otherwise explicitly stated to the contrary, all percentages in this disclosure refer to weight to weight percentages.

1. Introduction

The present disclosure provides methods and compositions for efficiently lysing red blood cells under isotonic, neutral pH conditions without deleterious effect on white blood cells in the whole blood samples. This method adds a hypertonic buffer to shrink the cells, and then uses a low concentration of fixative to lightly fix the cells and prevent transporters on the surface of RBCs from opening to compensate for changes in osmotic pressure. A hypotonic buffer is used to dilute the sample and restore the sample to an isotonic condition. Upon return to the isotonic condition, the WBCs swell back up, while the RBCs and platelets are not able to compensate and thus rupture. This is due to the fact that, unlike WBCs, which are better able to compensate for osmotic changes, the primary channel for compensating osmotic changes in the RBCs and resting platelets, the Gardos channel, is closed due to having constitutively low levels of internal calcium. Upon fixation, the aquaporins on the RBC and platelet membranes are crosslinked and the Gardos channels are unable to reopen even when the amount of calcium needed for activation is present. As a result, upon restoring to isotonic condition, red cells cannot swell back to their normal size and rupture. In addition, during the hypertonic period, the higher salt concentration outside also begins to equilibrate with the internal concentration at a faster rate in RBCs and further enables lysis.

Accordingly, the method disclosed herein, includes loading the red blood cells with a fixative under conditions wherein the solute concentration is greater than the solute concentration of whole blood and lysing the loaded red blood cells under conditions wherein the solute concentration is substantially the same as the solute concentration of the whole blood. The method provides for efficient RBC lysis within a relatively short time.

2. Methods

Raising Solution Tonicity and Fixing Cells

The method of the disclosure comprises contacting a sample comprising red blood cells and white blood cells with a first buffer comprising a fixative. The first buffer has a solute concentration that is greater than the solute concentration of the sample. This step is to raise the tonicity of the sample and lightly fix the cells. This first buffer is referred to here as the "RBC lysis buffer" or the "RBC demolition buffer." The term "solute" used throughout this disclosure refers to any substance that is dissolved in water, for example, salts. Any salt that is suitable for preparing biological material can be used in this invention. The RBC lysis buffer comprises a salt solution comprising one or more salts and the concentration of the total salts could vary, so long as it is greater than the solute concentration of whole blood. Typically the solute concentration of the blood is the equivalent of 1×PBS or 0.8-0.9% of NaCl. In some embodiments, the salt concentration can range from 150 mM to 600 mM, e.g., from 260 mM to 350 mM, or from 280 mM to 400 mM, or about 323 mM. Non-limiting examples of salts that can be used for the RBC lysis buffer include sodium chloride, potassium chloride and combinations thereof. In some embodiments, the salt is sodium chloride and is present in the RBC lysis buffer in a concentration of about 300 mM. In some embodiments, the RBC lysis buffer comprises 2× phosphate buffered saline ("PBS"), which comprises about 314 mM NaCl, 9 mM KCl, and 20 mM phosphate buffer, pH 7.4. In some embodiments, the hypertonic buffer is about 1-3×PBS, e.g., about 2.5×, or about 3×PBS.

The fixatives used in the RBC lysis buffer can be any fixatives that can cause crosslinking of proteins on the cell membrane. The fixatives used in this disclosure are present in a relatively low concentration such that it does not cause cell death yet is able to permeablize cell membrane to allow solute from the RBC demolition buffer to rapidly cross the membrane to reach inside the cell. Suitable fixative include formaldehyde, including formalin. The concentration of the fixative in the RBC demolition buffer can be in a range from 0.5% to 10%, e.g., from 5% to 7%, from 2% to 5%, from 3% to 4%, or about 3.2%.

The RBC lysis buffer may also comprise a calcium chelator. The calcium chelator removes calcium from the blood, which is required to activate the Gardos channels. As a result, the red blood cells lose the ability to swell back when they are subjected to hypotonic or isotonic conditions and thus will rupture. The reduced serum calcium also reduces cellular activation due to changes in osmotic pressures, which is characteristic of monocytes. Any calcium chelator can be used for the method. Non-limiting examples of calcium chelator include K3-EDTA, EDTA, EGTA, TPEN, and BAPTA. The calcium chelator can be present in a concentration ranging from 0.01 mM to 20 mM, e.g., from 10 mM to 15 mM, from 0.1 mM to 10 mM, from 1 mM to 5 mM, from 4 mM to 12 mM, e.g., about 10 mM in the RBC lysis buffer. The calcium chelator can also be a mixture of two or more aforementioned calcium chelators.

The pH of the RBC lysis buffer can affect the titrations for both fixatives and the salts in the buffer. The pH of the RBC lysis buffer is typically within the range from about 6.5 to about 8.5. In a preferred embodiment, the pH is the standard physiological pH, i.e., about 7.4.

In some embodiments, the salts (typically in the form of a salt solution, also referred to as a hypertonic saline), the fixatives, and/or the calcium chelators are mixed in the RBC lysis buffer and added to the sample simultaneously. In some embodiments, the salts, the fixative, and/or the calcium are added sequentially to the sample, in that order. In some embodiments, the salts and fixatives are added together to the sample followed by the addition of the calcium chelators.

The volume of the RBC lysis buffer required is dependent on the sample volume and the solute concentration of the RBC lysis buffer. In general, the higher solute concentration of the RBC lysis buffer, the lower volume of the RBC lysis buffer is required for the loading step and the lower volume of the hypotonic buffer is required to bring the mixture to an isotonic state. In some cases, the loading step includes mixing the RBC lysis buffer in a 1:1 volume ratio with the whole blood sample.

The contacting step of the method may further comprise the step of incubating the first mixture, which is formed by adding the RBC lysis buffer to the sample comprising red blood cells and white blood cells for a period of time. In general, a lower volume of more concentrated RBC lysis buffer and/or larger volume of balanced dilution buffer requires less incubation time. In some embodiments, the incubation of the first mixture lasts from about 0.5 minutes to about 20 minutes, e.g., about 45 seconds to about 10 minutes.

The concentrations of the various components in the first mixture, i.e. salt, fixatives and calcium chelator, must be within a reasonable operating range so that the red blood cells are sufficiently prepared to be lysed in subsequent steps as described below. In general, low fixative concentrations may result in insufficient RBC lysis and high fixative concentrations could potentially damage cells. The inventors have discovered that a concentration of the fixative in the first mixture that is in the range of about 1%-3%, e.g., about 1.25%-2.5%, or about 1-2%, generally produces good RBC lysis; although the performance tapers at either end of the concentration range. In preferred embodiments, the fixative is at a concentration ranging from about 1.6% to about 1.8%. The calcium chelator is present at a concentration of about 3 mM-7 mM, e.g., 5 mM. The first mixture may have a salt concentration equivalent to the salt concentration in 1.2-1.8×PBS, e.g., about 1.5×PBS.

Restoring Sample Mixture to Isotonic Conditions

After the sample is treated with the first buffer as described above, a second buffer is added to the first mixture comprising the cells and the RBC lysis buffer to form an isotonic, second mixture. The second buffer typically has a salt concentration that is about the same as the solute concentration in whole blood. In some embodiments, the second buffer comprises the same salt or salts as the first buffer. The volume and concentration of second buffer may vary, so long as adding the second buffer can restore the solute concentration in the second mixture to a level that is substantially the same as the solute concentration of the sample comprising red blood cells and white blood cells before the raising of the solution tonicity, or to a level that is substantially the same as the solute concentration of 1×PBS. The second mixture having such solute concentration is referred to as an isotonic mixture and the cells are now in an isotonic condition. In some embodiments, the second buffer is 0-1×PBS, e.g., 0.5-1×PBS, 0.7-0.9×PBS, 0.9-1×PBS, or about 0.9×PBS, or about 1×PBS. In some embodiments, the ratio between the volume of the second buffer added and the volume of the first mixture is at least 1:1, e.g., at least 2:1, at least 3:1, at least 4:1, or at least 5:1. In general, the higher the solute concentration of the second buffer, the larger volume of the buffer may be required to add to the first mixture in order to form an isotonic, second mixture.

In some embodiments, the second buffer may further comprise other components that are typically used for preparing biological samples, e.g., fetal bovine serum ("FBS"). In some cases, the second buffer is the same buffer that is used to wash the sample and prepare the sample for a particular assay. For example, it can be a buffer comprising 1×PBS plus FBS or BSA, or the L&L/Solastra wash buffer from Beckman Coulter.

The pH of the second buffer is typically within the range of about 7.0-about 8.0, e.g., about 7.4.

Optionally, the method further includes incubating the second mixture for a time period of between about 0.5 minute and about 20 minutes. The second mixture typically comprises about 0.01% to 2% fixatives, e.g., about 0.5% to 1.5%, or about 0.8% to about 1.2%.

Accordingly, this invention also provides a method of processing a whole blood sample by forming a first mixture consisting essentially of a sample of whole blood, a fixative, a hypertonic saline, and a calcium chelator. The solute concentration in the hypertonic saline, as well as the formed first mixture, is greater than the solute concentration of the whole blood. Any of the embodiments described above can also be included for this aspect of the invention.

Analysis or Storage

Upon completion of RBC lysis, the white blood cells in the sample are immersed in a solution in which the salt, fixatives and other parameters are appropriate for flow cytometry analysis. If washing is necessary, it can be centrifuged immediately after lysis. The sample can be stained with appropriate, detectable cell markers either before or after lysis, using methods well known in the art and subjected to flow cytometry analysis.

The sample can then be left in this solution for as long as desired or necessary, subject only to the standard provisions and expectations for long-term sample stability once in storage buffer.

3. Kits

The disclosure also provides a kit for lysing red blood cells. This kit is also referred to as Red Blood Cell Demolition Kit ("RDK") throughout the disclosure. The kit allows the user to carry out the method steps as described above. In preferred embodiments, the kit comprises a first reagent ("reagent 1"), i.e., the RBC lysis buffer, which consists essentially of a hypertonic saline, about 3.2% formaldehyde, and about 10 mM EDTA; and a second reagent comprising about 0.9× to about 1×PBS. The salt concentration in the first reagent can range from 150 mM to 600 mM, e.g., from 260 mM to 350 mM, or from 280 mM to 400 mM, or about 323 mM. In one particular embodiment, the hypertonic saline has a salt concentration of about 323 mM and has a pH 7.4. In some embodiments, the hypertonic saline is about 2.5× or about 2×PBS. In another particular embodiment, the second reagent includes about 0.9×PBS.

4. Applications

The methods and kits in this disclosure are compatible with a number of existing flow cytometry analysis applications. In one case, the methods and kits are used in dried-B-cell-antibody panels (Beckman Coulter). RBC demolition buffer can be added to whole blood samples placed in the dried-B-cell-antibody panel tubes and a hypotonic buffer is then added to restore the mixture to an isotonic state as described above. The red blood cells in the whole blood are lysed as a result and the sample can be stained and analyzed by flow cytometry.

The methods and kits in this disclosure can also be used in conjunction with L&L washing, which is commonly used for Kappa/Lambda staining. Red blood cells in the whole blood sample can be lysed with the wash buffer used in the L&L washing procedure itself, following incubation with the RDK. The treated sample is then rapidly centrifuged and decanted. In one particular embodiment, the wash buffer comprises 1×PBS and 2% FBS. In general, by using the L&L wash buffer as the buffer for the lysing step, it shortens the sample preparation time from more than one hour to about 15-20 minutes.

5. Exemplary Embodiments

Embodiment 1. A method of lysing red blood cells comprising: contacting a sample comprising red blood cells and white blood cells with a first buffer comprising a fixative, wherein the solute concentration of the first buffer is greater than the solute concentration of the sample, and wherein the sample and the first buffer form a first mixture; adding a second buffer to the first mixture to form a second mixture, wherein the solute concentration in the second mixture is at least 90%, of the solute concentration of the sample and whereby the red blood cells in the sample are lysed.

Embodiment 2. The method of embodiment 1, wherein the sample is whole blood.

Embodiment 3. The method of embodiment 1, further comprising, before the step of adding the second buffer, adding a calcium chelator, wherein the calcium chelator blocks calcium-dependent transport in the red blood cells by chelating calcium.

Embodiment 4. The method of embodiment 1, wherein the first buffer further includes a calcium chelator, wherein the calcium chelator blocks calcium dependent transport in the red blood cells.

Embodiment 5. The method of any of embodiments 1-4, wherein the contacting step further includes incubating the first mixture for a period between 0.5 minutes and 20 minutes.

Embodiment 6. The method of embodiment 1, wherein the method step further includes incubating the second mixture for a second period between 0.5 minutes and 20 minutes.

Embodiment 7. The method of any of embodiments 1-6, wherein the second buffer includes 0× to 1×PBS.

Embodiment 8. The method of any of embodiments 1-7, wherein the first mixture includes 0.5-3% formaldehyde, 0.5-20 mM EDTA, and 1.2-1.8× phosphate buffered saline (PBS).

Embodiment 9. The method of embodiment 4, wherein the first buffer includes 0.5% to 10% formaldehyde, 0.01 mM to 20 mM EDTA, and 150 mM to 600 mM salt at a pH of 6.5 to 8.5.

Embodiment 10. The method of embodiment 9, wherein the first buffer includes 1-3×PBS.

Embodiment 11. The method of any of embodiments 1-10, wherein the contacting step includes mixing the first buffer with the sample in a volume ratio that ranges from 0.2:1 to 1:1.

Embodiment 12. A method of processing a whole blood sample comprising: forming a first mixture comprising a sample of whole blood, a fixative, a hypertonic saline, and a calcium chelator, wherein the solute concentration of the hypertonic saline is greater than the solute concentration of the whole blood; and adding a second buffer to the first mixture to form an isotonic second mixture.

Embodiment 13. The method of embodiment 12, wherein the first mixture includes 0.5-3% formaldehyde and 3-7 mM EDTA.

Embodiment 14. The method of embodiment 12 or 13, wherein the second mixture includes 0.01-2% formaldehyde.

Embodiment 15. The method of any of embodiments 12-14, wherein the second buffer is 0×-1×PBS.

Embodiment 16. The method of any of embodiments 12-15, further comprising staining cells of the first or the second mixture and introducing the stained cells after lysis into a cytometer.

Embodiment 17. A red cell lysis kit comprising: a first reagent comprising a hypertonic saline, 0.5% to 10% formaldehyde, and 0.01 mM to 20 mM EDTA, wherein the solute concentration of the first reagent is greater than the solute concentration of a whole blood sample; and a second reagent including 0× to 1×PBS.

Embodiment 18. The red cell lysis kit of embodiment 17, wherein the hypertonic saline has a salt concentration of 150 mM to 600 mM and is at pH of 6.5 to 8.5.

Embodiment 19. The red cell lysis kit of embodiment 17 or 18, wherein the second reagent includes 0×-1×PBS.

EXAMPLES

The following examples are offered to illustrate, but not to limit the claimed invention.

Example 1

In this example, the RBS demolition buffer was composed of: 1) 3.2% Formaldehye, 2) 2×PBS (roughly 274 mM NaCl, 5.4 mM KCl, and 20 mM Na2HPO4, and 3.6 mM KH2PO4, pH 7.4), and 3) 10 mM K3-EDTA. The buffer was added to the whole-blood sample at a volume-to-volume ratio of 1:1, and then incubated for a time that was between ~45 sec and 10 minutes. The final concentration upon 1:1 dilution was: 1) 1.6% Formaldehyde, 2) 1.5×PBS, and 3) 5 mM K3-EDTA, and the actual concentrations of the buffer can be altered to allow for different volumes provided that they also result in these final concentrations. Upon dilution with 0.9× to 1×PBS or IsoFlow to anywhere greater than 4× the initial sample volume, the RBCs and resting platelets were completely lysed in about the same time frame as it was incubated with the first reagent (i.e., ~45 sec to 10 minutes, respectively). The volume may be further reduced and/or optimized at lower volumes if the solution is adjusted so as to provide a final salt concentration closer to 1×PBS. For general use, 0.9×PBS will function better to restore the final concentration than 1×PBS, though 1× works well in most cases and is more convenient.

Example 2

The methods and kits disclosed are compatible with a number of existing flow cytometry analysis applications. One of such applications is the dried-B-cell-antibody panel (Beckman Coulter). In one assay, 150 mL of RBC demolition buffer, i.e., the first reagent of the RDK was mixed with 50 mL of PBS to produce a 200 mL mixture. The mixture was added to the 100 mL blood post-staining. 1×PBS was used to restore the mixture to the isotonic state. In another assay, 200 μL of the RDK first reagent was added to 50 mL whole blood sample. After a two-minute incubation, 0.9× PBS was added to restore the mixture to isotonic state. In yet another assay, 150 μL of the RDK first reagent was added to 100 μL blood and 50 μL of antibodies and after incubation for 2 minutes, 0.9×PBS was added to restore the mixture to the isotonic state. The samples are then used for flow cytometry analysis.

In the case of L&L washing for Kappa/Lambda staining, the samples were lysed directly with wash buffer. Instead of washing with 3 rounds of gentle centrifugation and aspiration (taking about 45 min to wash, followed by 20 minutes of lysing), the sample was lysed with 1 min of RDK+PBS/2% FBS wash buffer and then rapidly centrifuged and decanted (taking around 5-6 min per wash). As a result, the sample preparation time was significantly reduced, i.e., from >60 min to ~15-20 minutes total.

Example 3

RBC Demolition Kit (RDK) was used for lysing RBCs in whole blood. All lyses were performed for exactly 10 min, which for the RDK consisted of 2 min of incubation with reagent 1, followed by 8 min with 1×PBS.

FIG. 1 is a 3-donor comparison of the RDK to a precedent buffer. The upper panel compares the CD45 vs. Side Scatter (SS) dot plots, while the lower panel demonstrates the respective Forward Scatter (FS) and SS profiles for each of their CD45 populations. All scatter profiles were consistent, and the results show that RBCs were fully lysed by the RDK in all cases. In the CD45 vs. SS plots, the population entitled "NonWBC" consists of RBCs and resting platelets, while the population between the NonWBC and CD45 gates consists of activated platelets. Activated platelets typically do not lyse by any method, though they may be reduced in some cases or will sometimes smear up into the CD45 population.

Figure 2:
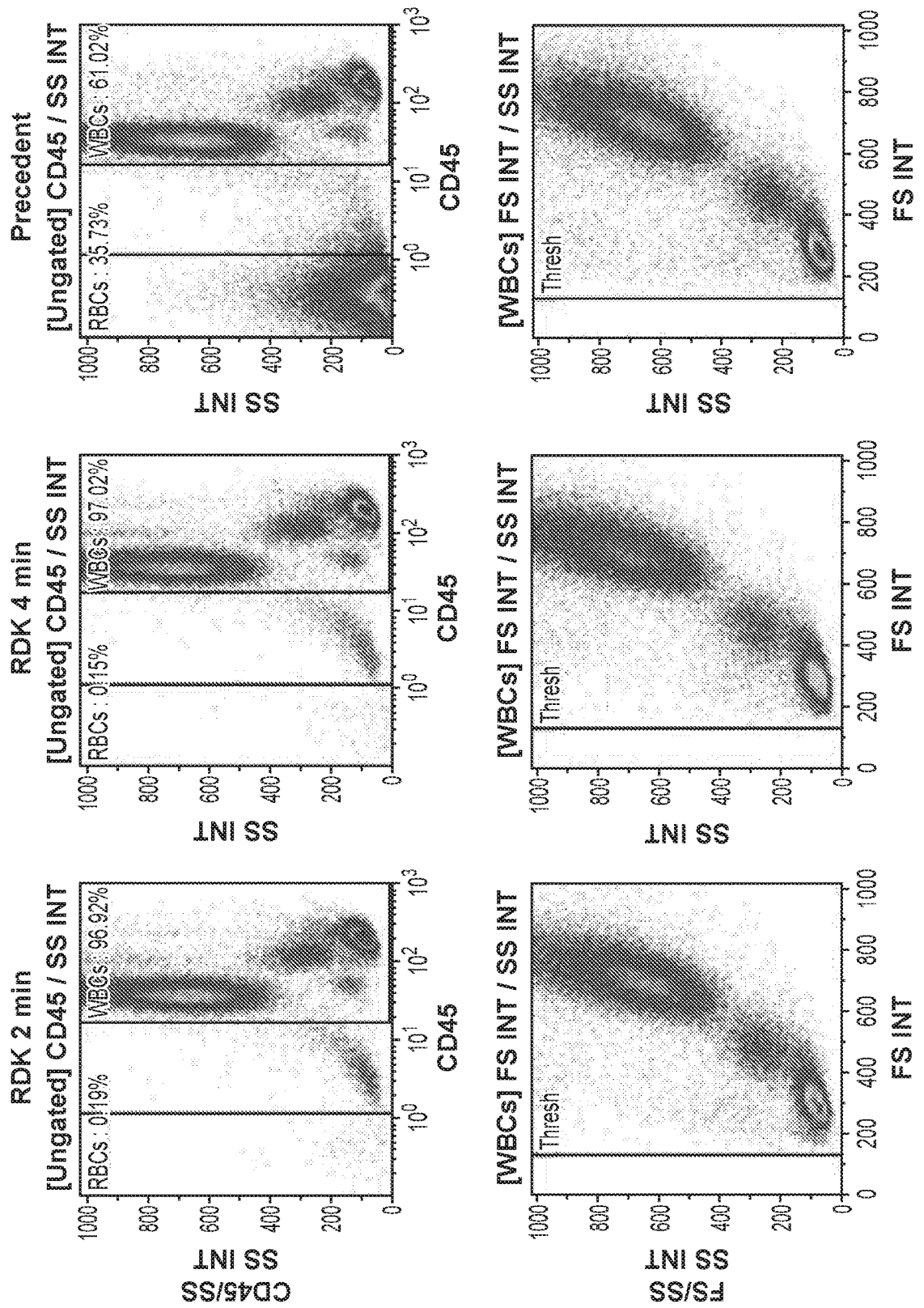
FIG. 2 shows the results of flow cytometry analysis of K3-EDTA blood that was lysed with RDK or the precedent buffer.

FIG. 2 is comparison of 2 and 4 min of incubation with RDK reagent 1 vs. incubation with the precedent buffer using EDTA blood. The upper panel is CD45 vs. SS, while the lower panel is FS vs. SS. The scatter profiles of the samples treated with the two methods were similar, and the results showed that RDK fully lysed the samples. There were no differences in the scatter profiles for 2 min vs. 4 min incubation time, either with RDK reagent or with the precedent buffer.

Figure 3:
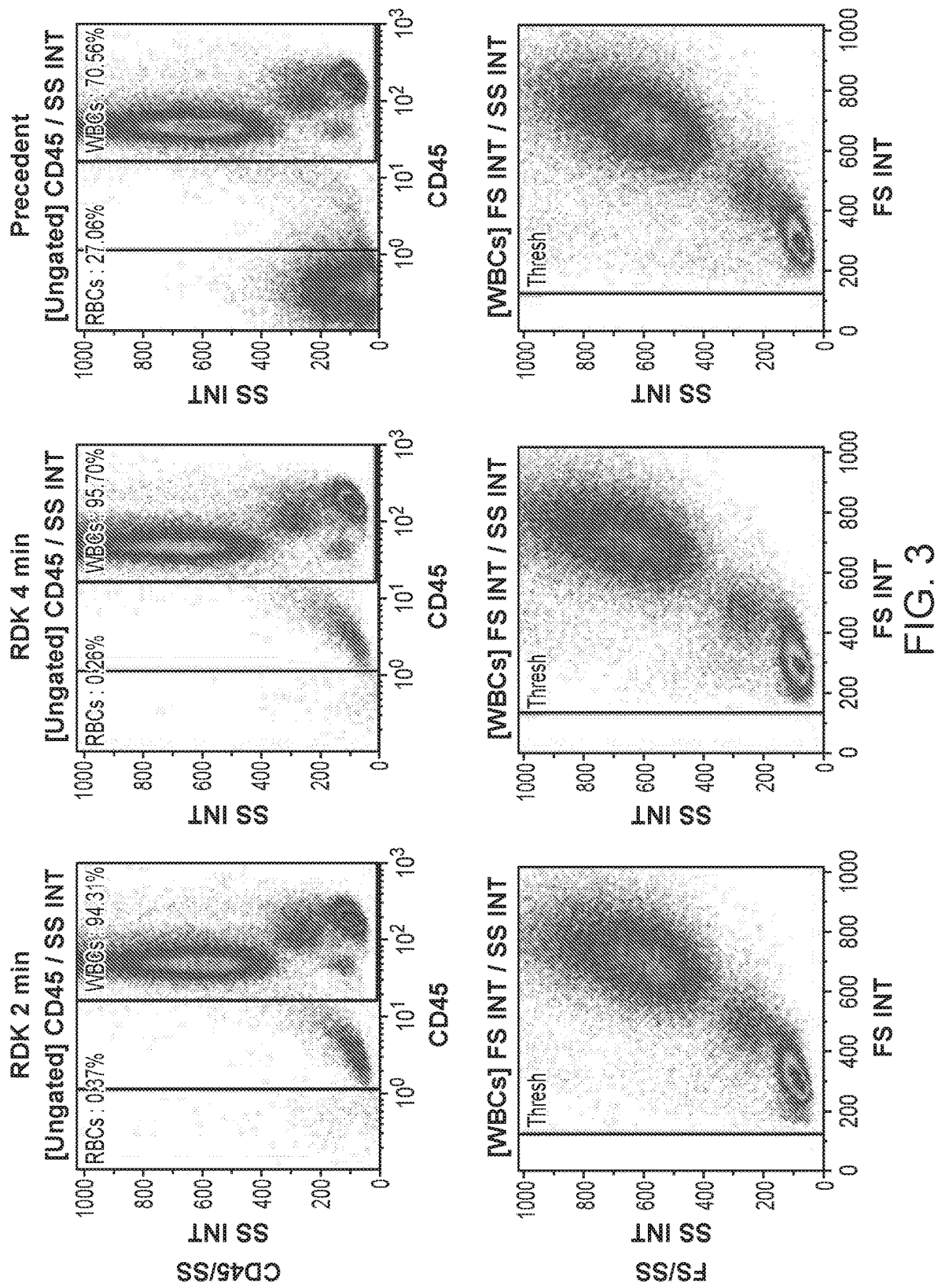
FIG. 3 shows the results of flow cytometry analysis of heparin blood that was lysed with RDK or the precedent buffer.

FIG. 3 is a comparison of 2 and 4 min of incubation with RDK reagent 1 vs. the precedent buffer using heparin blood, similar to FIG. 2. The scatter profiles were similar, and the RDK completely lysed the samples. There were no significant differences in the scatter profiles for samples that were incubated with the RDK reagent 1 or the precedent buffer for 2 minutes vs. incubated for 4 min.

Figure 4:
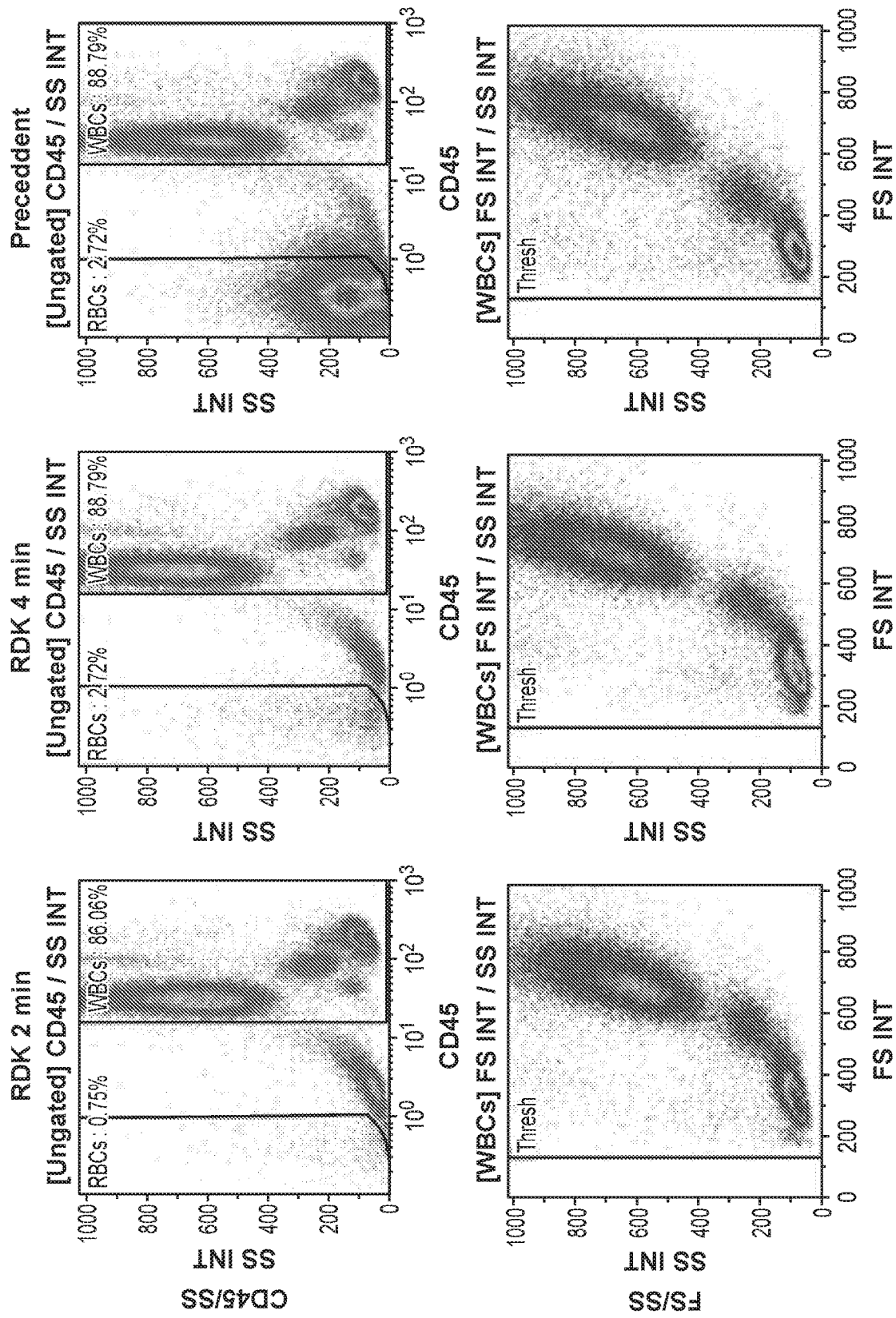
FIG. 4 shows the results of flow cytometry analysis of ACD blood that was lysed with RDK or the precedent buffer.

FIG. 4 is a comparison of 2 and 4 min of incubation with RDK reagent 1 vs. the precedent buffer using ACD blood, also similar to FIG. 2. The scatter profiles of the samples treated with the two methods were similar, and the results showed that RDK fully lysed the samples. There were no differences in the scatter profiles for 2 min vs. 4 min incubation time, either with RDK reagent or with the precedent buffer.

Figure 5:
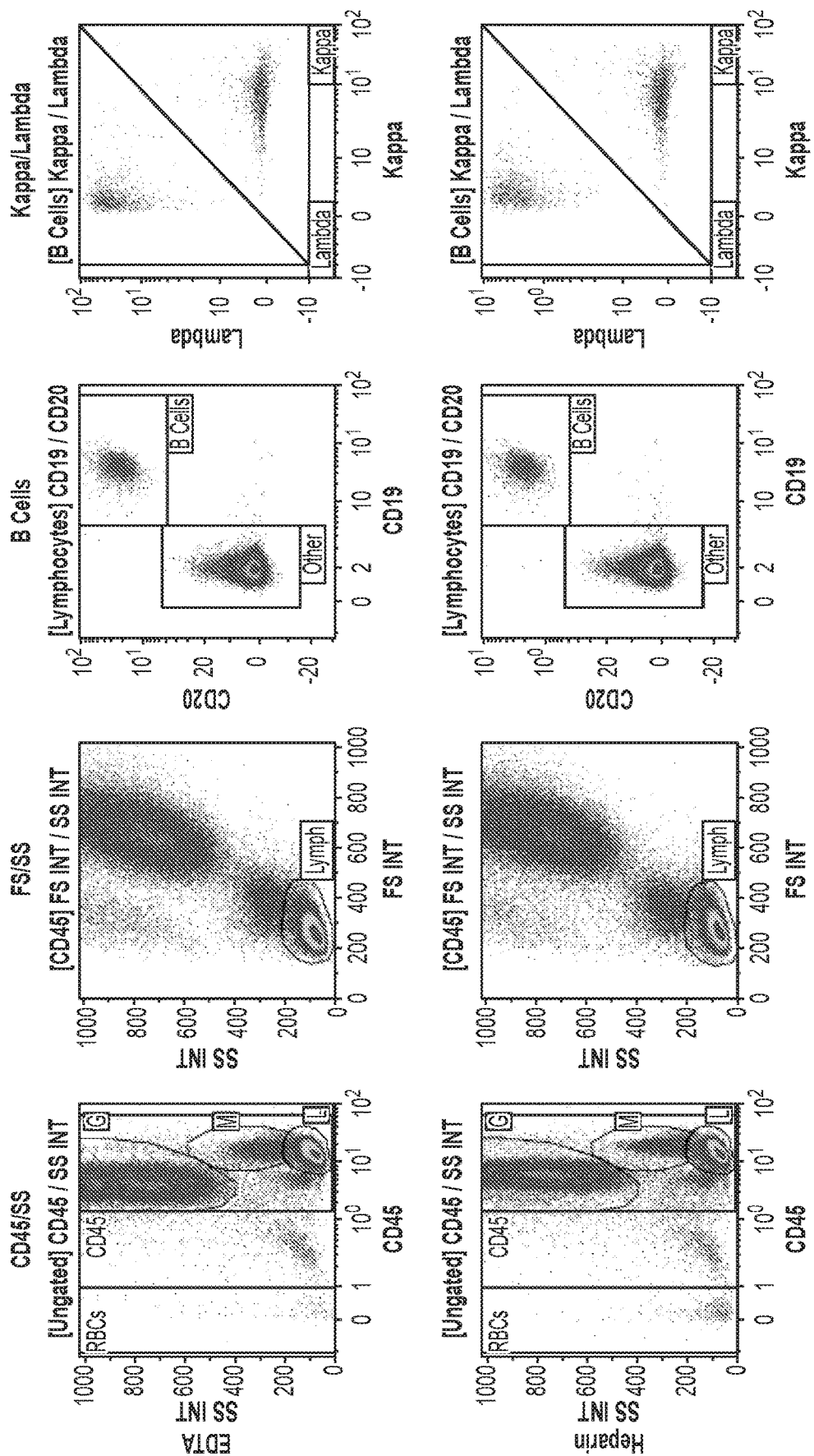
FIG. 5 shows the performance of lysing red blood cells using RDK in dried-B-cell-antibody panel tubes.
Figure 5:
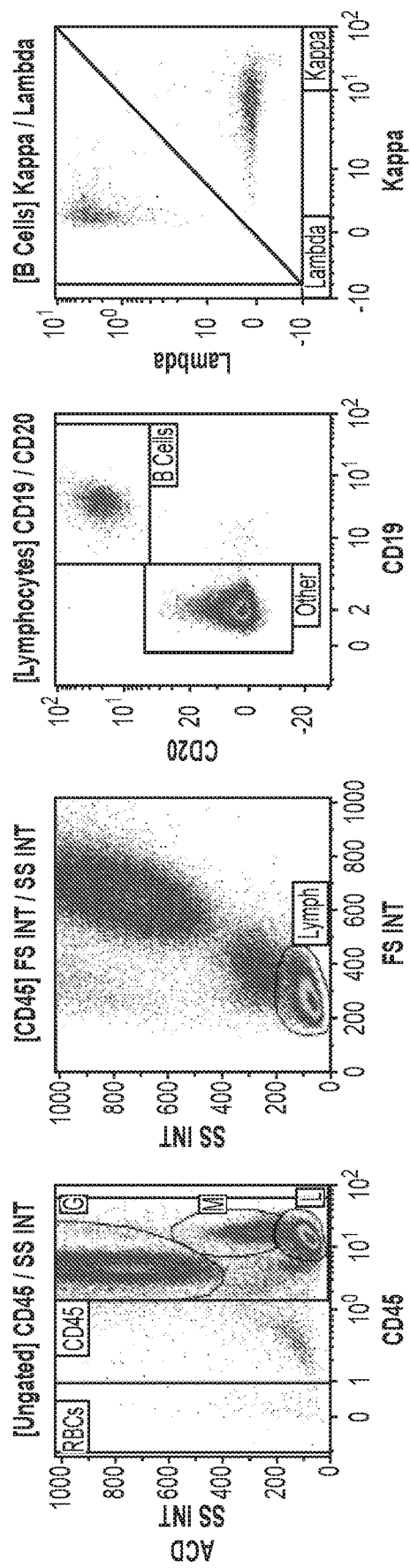

FIG. 5 is a demonstration of the performance of RDK with dried-B-cell-antibody tubes. From left to right, the gating workflow demonstrates CD45 vs. SS, FS vs. SS, CD19 vs. CD20 to gate B cells (using a Lymphocyte boolean gate consisting of all events within both Lymph and L), and finally the Kappa vs. Lambda signals for the B cell population. The upper panel is EDTA blood, while the middle panel is Heparin blood and the lower panel is ACD blood. The samples were first bulk washed 3× with PBS/2% FBS. The final volume was adjusted back to 1× the original sample volume using the wash buffer. 100 μL of the washed blood was added to each B cell dried-B-cell-antibody tube and incubated for 20 min to stain the cells. After incubation, the RBCs were lysed with RDK, washed 2× (including the RDK buffer as 1st wash), and then read on a flow cytometer. The scatter profiles for these samples looked good, and there was very little cell death as is seen with other lysis methods, which often result in the WBC populations shifting over to the lower forward scatter ("FS") region. The Kappa/Lambda staining worked very well.

Figure 6:
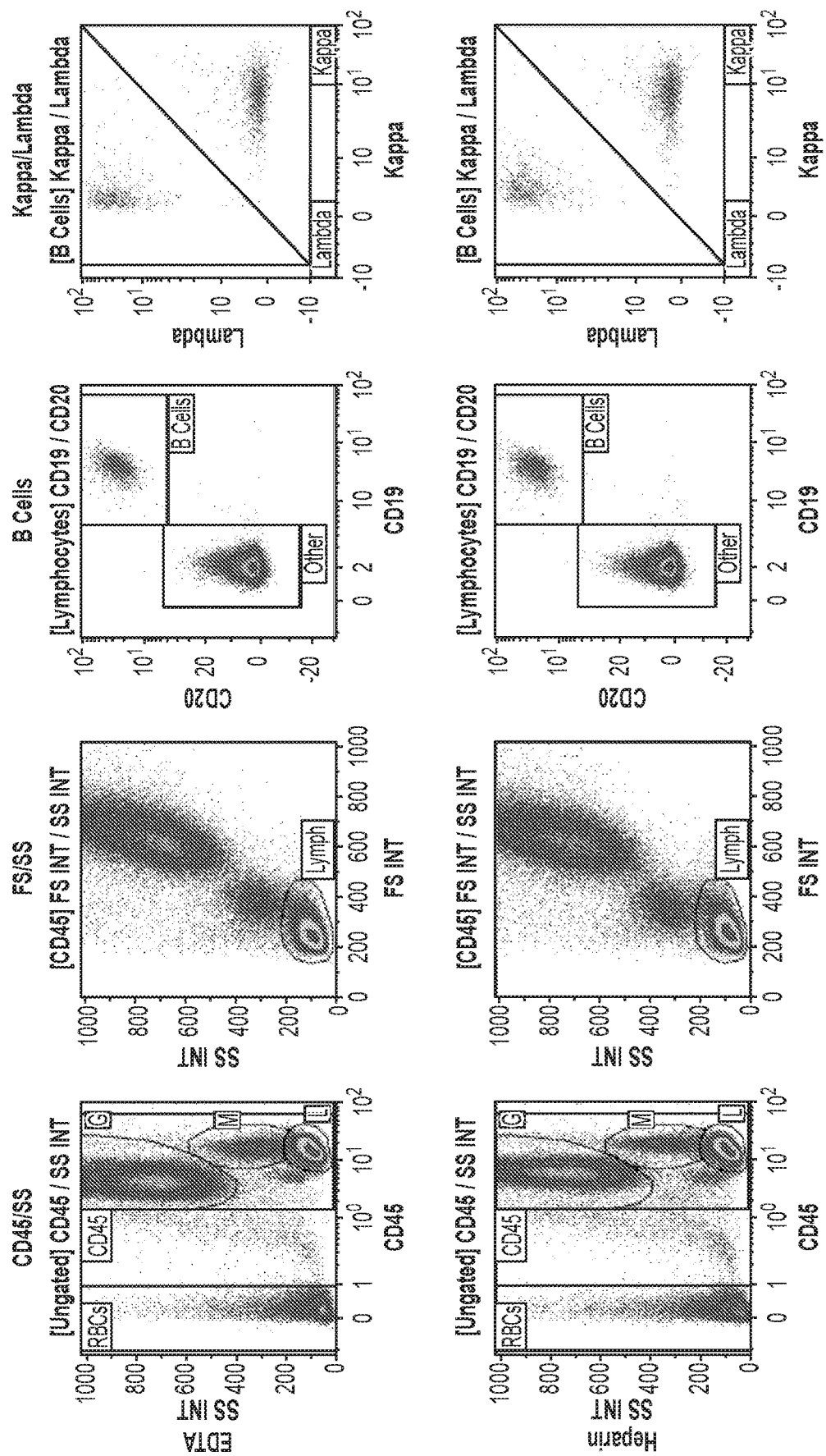
FIG. 6 shows the performance of lysing red blood cells using the precedent buffer with the wet B-cell Panel.
Figure 6:
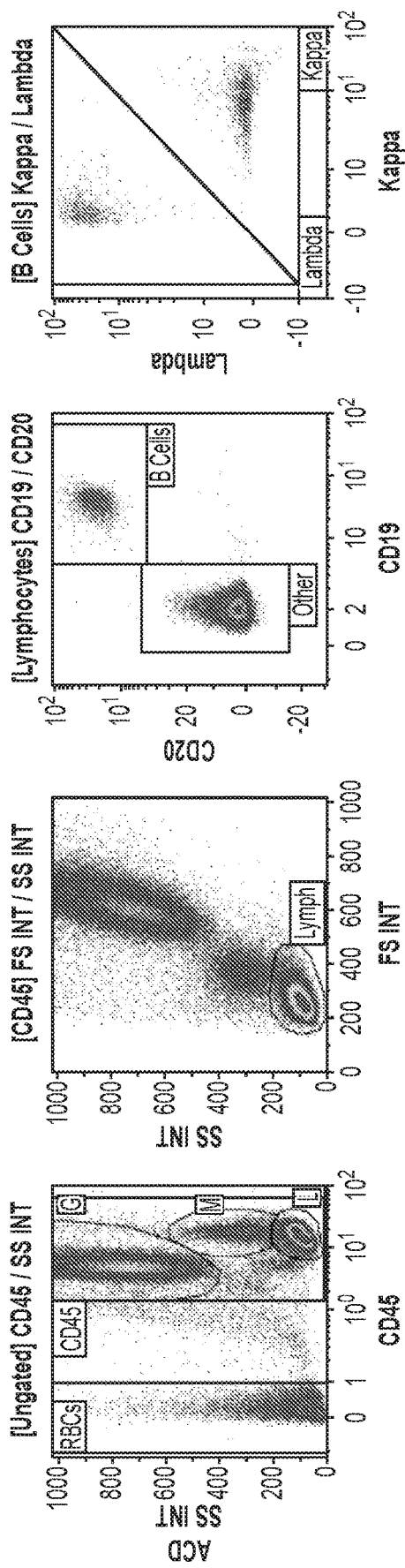

FIG. 6 shows the performance of the precedent buffer with the same panel using wet antibody reagents. RDK worked as well for lysing RBCs directly in the dried-antibody-panel tubes as the precedent buffer with the wet reagents. The RDK lysed the samples in the dried-antibody-panel tubes, regardless of the type of anticoagulant used. The performance of the RDK with samples stained using the dried-antibody panels, as seen in FIG. 5, was similar to the performance of the precedent buffer with samples stained using the wet B-cell panel, as seen in this figure. The workflow was the same for both FIG. 5 and FIG. 6, except that one the precedent buffer was used with wet antibodies, while the RDK was used using dried antibodies in the dried-B-cell-antibody tube. The precedent buffer was unable to lyse the sample in the dried-reagent tubes.

Figure 7:
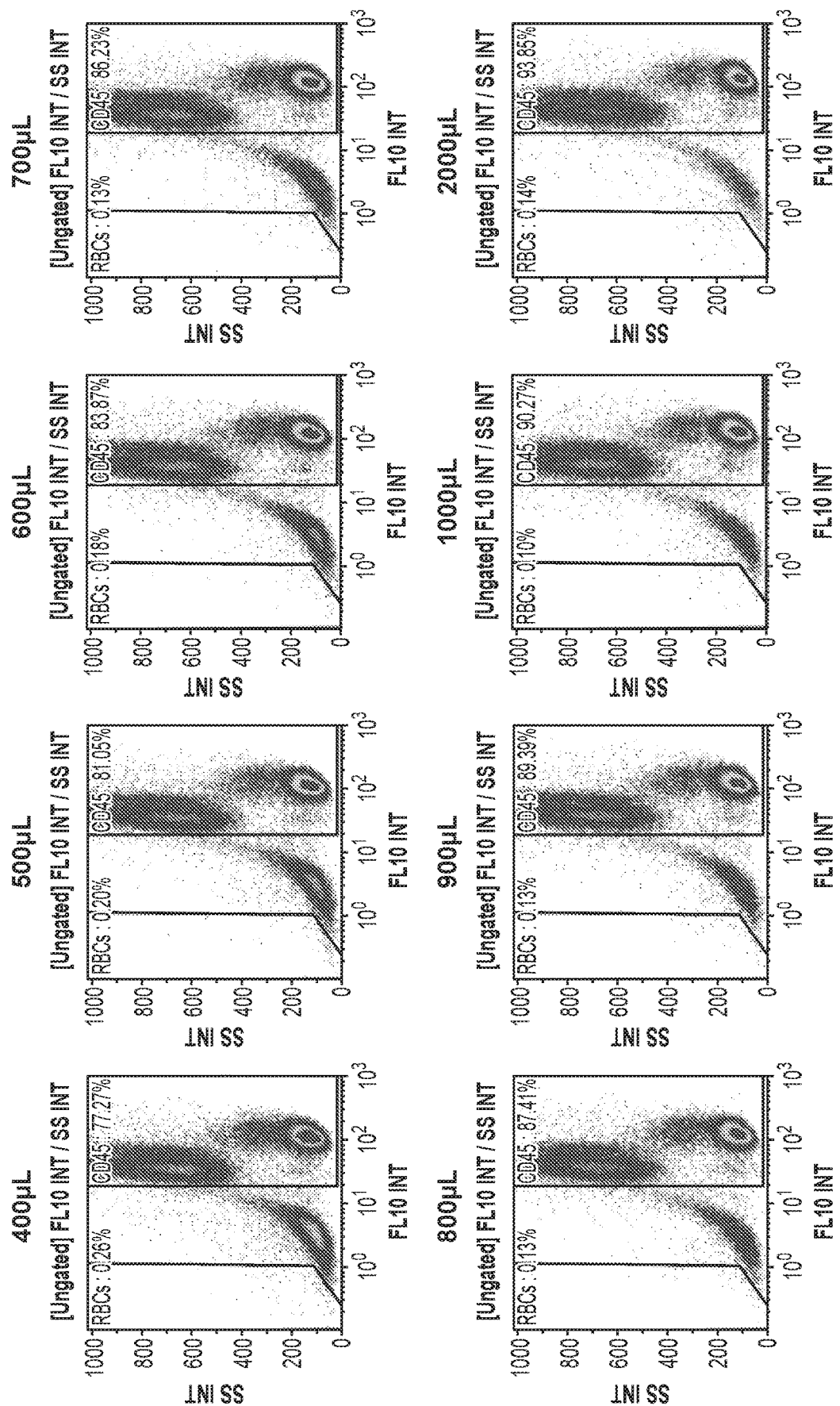
FIG. 7 shows results of the lysing RBCs using reduced volumes of 1×PBS.
Figure 8A:
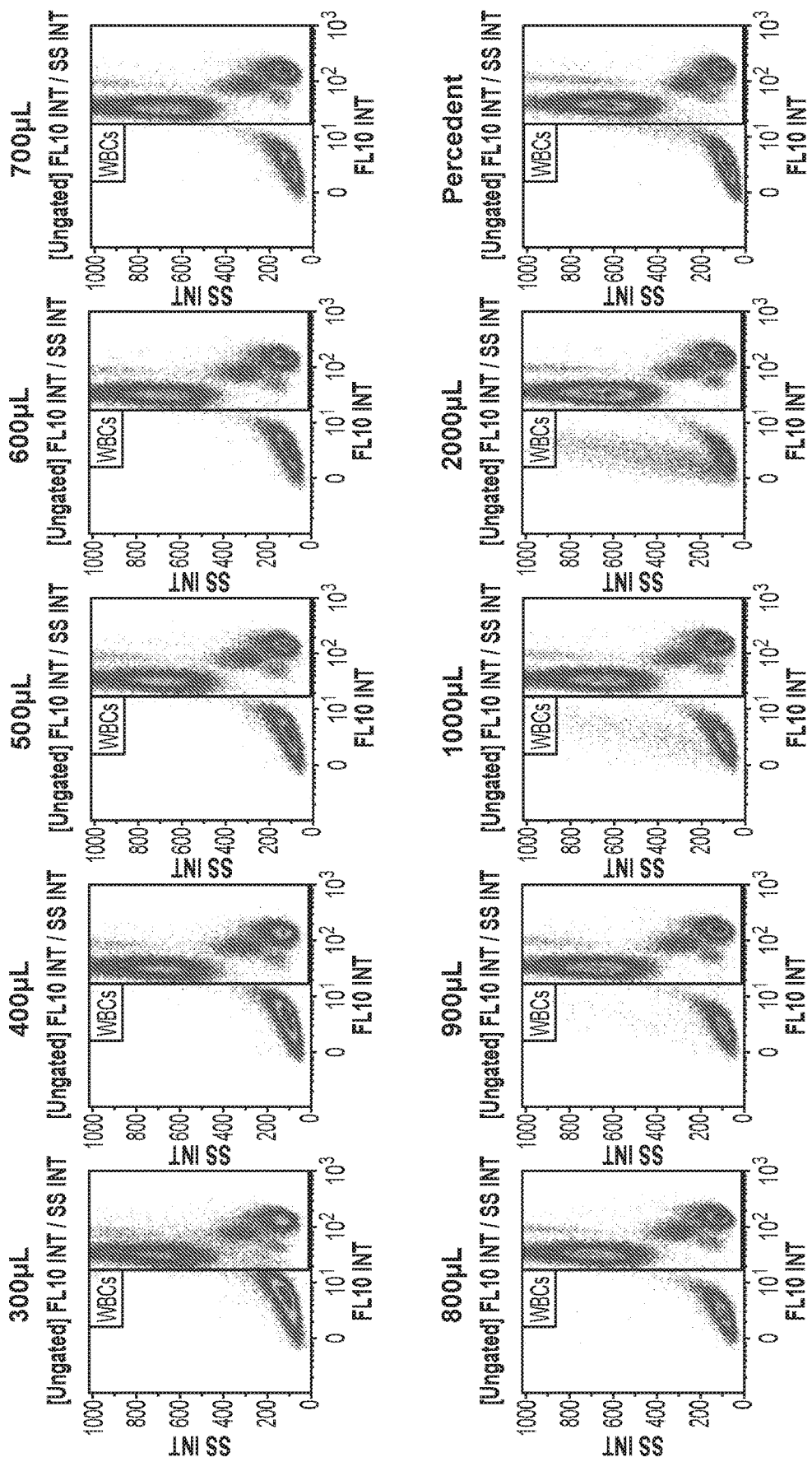
FIG. 8A-B show the results of lysing RBCs using reduced volumes of PBS, adjusted to a final 1× Concentration.
Figure 8B:
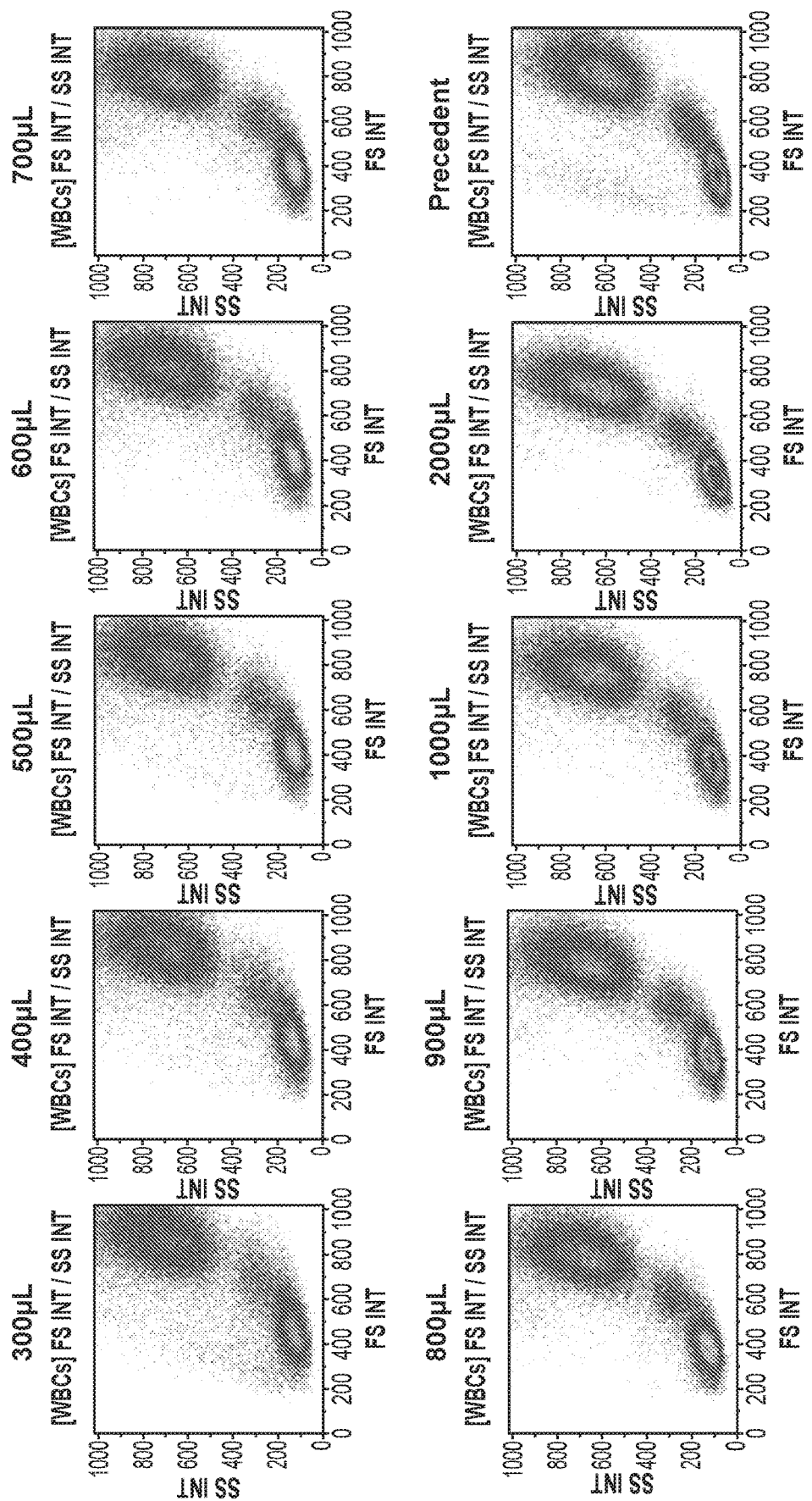

FIG. 7 shows RDK fully lysed red blood cells when even only 400 μL, of 1×PBS was used. Partial lysis was observed when the volume was further reduced to 300 μL. FIG. 7 demonstrates the lysis efficiency of the system with different volumes of 1×PBS used for the second buffer. The 400 µL sample represents 100 µL of blood mixed 1:1 with the RDK reagent for 2 min, followed by dilution in 400 µL of 1×PBS and incubation for 8 min. The 1000 µL sample represents 100 µL of blood mixed 1:1 with the RDK reagent for 2 min, followed by dilution in 1 mL of 1×PBS and incubation for 8 min. Partial lysis was observed when using 300 µL of 1×PBS for Buffer 2, but the lower effective limit for lysis with 1×PBS was 400 µL. These results were without washing. FIG. 8 demonstrates the lysis efficiency of the system with different volumes of Buffer 2, balanced to have a final concentration equivalent to 1×PBS. The 300 µL sample represents 100 µL of blood mixed 1:1 with the RDK reagent for 2 min, followed by dilution in 300 µL of 0.67×PBS and incubation for 8 min. The 1000 µL sample represents 100 µL of blood mixed 1:1 with the RDK reagent for 2 min, followed by dilution in 1 mL of 0.9×PBS and incubation for 8 min. These results were without washing. FIG. 8 shows the lysis of RBCs using smaller volumes of PBS adjusted so that the final concentration equals 1×PBS (i.e., 300 µL=+300 µL of 0.67×PBS, 400 µL=+400 µL of 0.75×PBS, etc.) Panel A consists of the CD45 vs. SS profiles, while Panel B consists of the FS vs. SS profiles. Panel A shows that the RDK was able to lyse RBCs completely in all volumes of the solutions, down to 300 µL, and around 500 µL appears to be the volume about which the best qualitative results were obtained. In this case, the 300 µL mixture consists of 100 µL blood, 100 µL RDK reagent 1, and 300 µL of 0.67×PBS. Panel B shows that, overall, the scatter profiles looked good, though the lower volumes got a little fuzzy, likely due to coincidence with RBC and platelet fragments. The fuzziness could be improved by reducing the sample acquisition rate, in turn reducing coincidence. The coincidence with the RBC and platelet fragments in unwashed samples would likely be an issue for all lysis buffers if they were able to lyse in such small volume ratios.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of lysing red blood cells comprising:
    contacting a sample comprising red blood cells and white blood cells with a first buffer comprising about 0.5% to 10% formaldehyde, 0.01 mM to 20 mM ethylenediaminetetraacetic acid (EDTA) and 150 mM to 600 mM salt at a pH of 6.5 to 8.5,
    wherein the solute concentration of the first buffer is greater than the solute concentration of the sample, and wherein the sample and the first buffer form a first mixture;
    adding a second buffer comprising 0.5× to 1× phosphate-buffered saline (PBS) to the first mixture to form a second mixture, wherein the solute concentration in the second mixture is at least 90% of the solute concentration of the sample and wherein the red blood cells in the sample are lysed.

2. The method of claim 1, wherein the sample is whole blood.

3. The method of claim 1, wherein the contacting step further includes incubating the first mixture for a period between 0.5 minutes and 20 minutes.

4. The method of claim 1, wherein the method step further includes incubating the second mixture for a second period between 0.5 minutes and 20 minutes.

5. The method of claim 1, wherein the first mixture comprises about 0.5-3% formaldehyde, 0.5-20 mM EDTA, and 1.2-1.8×PBS.

6. The method of claim 1, wherein the first buffer includes 1-3×PBS.

7. The method of claim 1, wherein the contacting step includes mixing the first buffer with the sample in a volume ratio that ranges from 0.2:1 to 1:1.

8. A method of processing a whole blood sample comprising:
    forming a first mixture comprising a sample of whole blood, about 0.5% to 10% formaldehyde, a hypertonic saline having a salt concentration of 150 mM to 600 mM and is at pH of 6.5 to 8.5, and 0.01 mM to 20 mM ethylenediaminetetraacetic acid (EDTA),
    wherein the solute concentration of the hypertonic saline is greater than the solute concentration of the whole blood; and
    adding a second buffer comprising 0.5× to 1× phosphate-buffered saline (PBS) to the first mixture to form an isotonic second mixture.

9. The method of claim 8, wherein the first mixture comprises 0.5-3% formaldehyde and 3-7 mM EDTA.

10. The method of claim 8, wherein the second mixture includes 0.01-2% formaldehyde.

11. The method of claim 8, further comprising staining the whole blood cells of the first mixture or white blood cells after lysis of the red blood cells of the second mixture and introducing the stained cells into a cytometer.

12. A red cell lysis kit comprising:
    a first reagent comprising a hypertonic saline, 0.5% to 10% formaldehyde, and 0.01 mM to 20 mM ethylenediaminetetraacetic acid (EDTA),
    wherein the solute concentration of the first reagent is greater than the solute concentration of a whole blood sample; and
    a second reagent including 0.5× to 1× phosphate-buffered saline (PBS),
    wherein the hypertonic saline has a salt concentration of 150 mM to 600 mM and is at pH of 6.5 to 8.5.

* * * * *